United States Patent
Shinoda

(10) Patent No.: US 10,212,315 B2
(45) Date of Patent: Feb. 19, 2019

(54) IMAGE PROCESSING APPARATUS, PRINTER APPARATUS, AND IMAGE PROCESSING METHOD

(71) Applicant: Panasonic Intellectual Property Management Co., Ltd., Osaka (JP)

(72) Inventor: Masayo Shinoda, Tokyo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 103 days.

(21) Appl. No.: 15/431,772

(22) Filed: Feb. 14, 2017

(65) Prior Publication Data
US 2017/0259599 A1 Sep. 14, 2017

(30) Foreign Application Priority Data
Mar. 8, 2016 (JP) .................. 2016-044888

(51) Int. Cl.
| | |
|---|---|
| *A61K 8/02* | (2006.01) |
| *A61Q 1/02* | (2006.01) |
| *B41M 1/10* | (2006.01) |
| *B44C 1/10* | (2006.01) |
| *G06T 7/90* | (2017.01) |

(Continued)

(52) U.S. Cl.
CPC ........... *H04N 1/628* (2013.01); *A45D 44/002* (2013.01); *A61K 8/0204* (2013.01); *A61Q 1/025* (2013.01);

(Continued)

(58) Field of Classification Search
CPC ........ B41M 3/008; B41M 1/10; B41J 3/4075; B41J 2/01; B41J 29/393; H04N 1/60;
(Continued)

(56) References Cited

U.S. PATENT DOCUMENTS

| | | | |
|---|---|---|---|
| 6,737,449 B1 | 5/2004 | Yatake | |
| 7,517,571 B2 * | 4/2009 | Funke | B44C 1/1758 428/195.1 |

(Continued)

FOREIGN PATENT DOCUMENTS

| | | |
|---|---|---|
| JP | 10-046073 | 2/1998 |
| JP | 2003-044837 | 2/2003 |

(Continued)

*Primary Examiner* — Nicholas Pachol
(74) *Attorney, Agent, or Firm* — Greenblum & Bernstein, P.L.C.

(57) ABSTRACT

An image processing apparatus controls an operation of a printer apparatus that prints an image on a sheet being attachable to skin. The image processing apparatus includes: an image acquirer that acquires a skin image; an image analyzer that extracts, from the skin image, a discolored region differing in color from surrounding skin by at least a predetermined level, and color of the surrounding skin; a print type determiner that determines, based on at least one of color and size of the discolored region, a print type that includes at least one of use/nonuse of a base material containing a white pigment, a particle shape of a print material used in the printing, a scheme of the printing, and use/nonuse of lamé powder; and a printing controller that outputs, to the printer apparatus, image data having a content of printing a print material in the surrounding color, on a region corresponding to the discolored region in the sheet, and controls an operation of the printer apparatus according to the determined print type.

10 Claims, 7 Drawing Sheets

(51) Int. Cl.
*H04N 1/00* (2006.01)
*H04N 1/60* (2006.01)
*H04N 1/62* (2006.01)
*A45D 44/00* (2006.01)
*B41F 33/00* (2006.01)
*B41J 3/407* (2006.01)

(52) U.S. Cl.
CPC ......... *B41F 33/0027* (2013.01); *B41J 3/4075* (2013.01); *B41M 1/10* (2013.01); *B44C 1/105* (2013.01); *G06T 7/90* (2017.01); *H04N 1/00023* (2013.01); *H04N 1/00034* (2013.01); *H04N 1/60* (2013.01); *A45D 2044/007* (2013.01); *G06T 2207/10024* (2013.01); *G06T 2207/30201* (2013.01)

(58) Field of Classification Search
CPC .... A61K 8/0204; A45D 44/002; A61Q 1/025; G06T 7/90; B41F 33/0027
See application file for complete search history.

(56) References Cited

U.S. PATENT DOCUMENTS

| | | | |
|---|---|---|---|
| 8,036,448 B2* | 10/2011 | Gildenberg | A61B 34/30 382/100 |
| 2002/0110672 A1* | 8/2002 | Muratore-Pallatino | B32B 7/06 428/195.1 |
| 2014/0020702 A1* | 1/2014 | Eguchi | A45D 40/00 132/200 |

FOREIGN PATENT DOCUMENTS

| | | |
|---|---|---|
| JP | 2005-126729 | 5/2005 |
| JP | 2012-086475 | 5/2012 |
| JP | 2012-203425 | 10/2012 |
| JP | 2015-043836 | 3/2015 |

\* cited by examiner

FIG. 7 610

| COLOR DEPTH IS LESS THAN FIRST PREDETERMINED VALUE | DETERMINE PRINTING OF COLOR MATERIAL IN SURROUNDING COLOR |
|---|---|
| COLOR DEPTH IS EQUAL TO OR GREATER THAN FIRST PREDETERMINED VALUE | DETERMINE PRINTING OF WHITE-COLOR BASE MATERIAL+COLOR MATERIAL IN SURROUNDING COLOR |

FIG. 8 620

| AREA IS LESS THAN SECOND PREDETERMINED VALUE | SELECT PRINT MATERIAL OF SPHERICAL CRYSTAL/INDEFINITELY-SHAPED CRYSTAL |
|---|---|
| COLOR DEPTH IS LESS THAN THIRD PREDETERMINED VALUE | SELECT PRINT MATERIAL OF SPHERICAL CRYSTAL/INDEFINITELY-SHAPED CRYSTAL |
| AREA IS EQUAL TO OR GREATER THAN SECOND PREDETERMINED VALUE | SELECT PRINT MATERIAL OF PLATE CRYSTAL |
| COLOR DEPTH IS EQUAL TO OR GREATER THAN THIRD PREDETERMINED VALUE | SELECT PRINT MATERIAL OF PLATE CRYSTAL |

FIG. 9 630

| AREA IS LESS THAN FOURTH PREDETERMINED VALUE | SELECT INKJET PRINTING |
|---|---|
| AREA IS EQUAL TO OR GREATER THAN FOURTH PREDETERMINED VALUE | SELECT SPRAY PRINTING/RELIEF PRINTING |

FIG. 10 640

| AREA IS EQUAL TO OR GREATER THAN FIFTH PREDETERMINED VALUE | DETERMINE PRINTING OF LAMÉ POWDER |
|---|---|

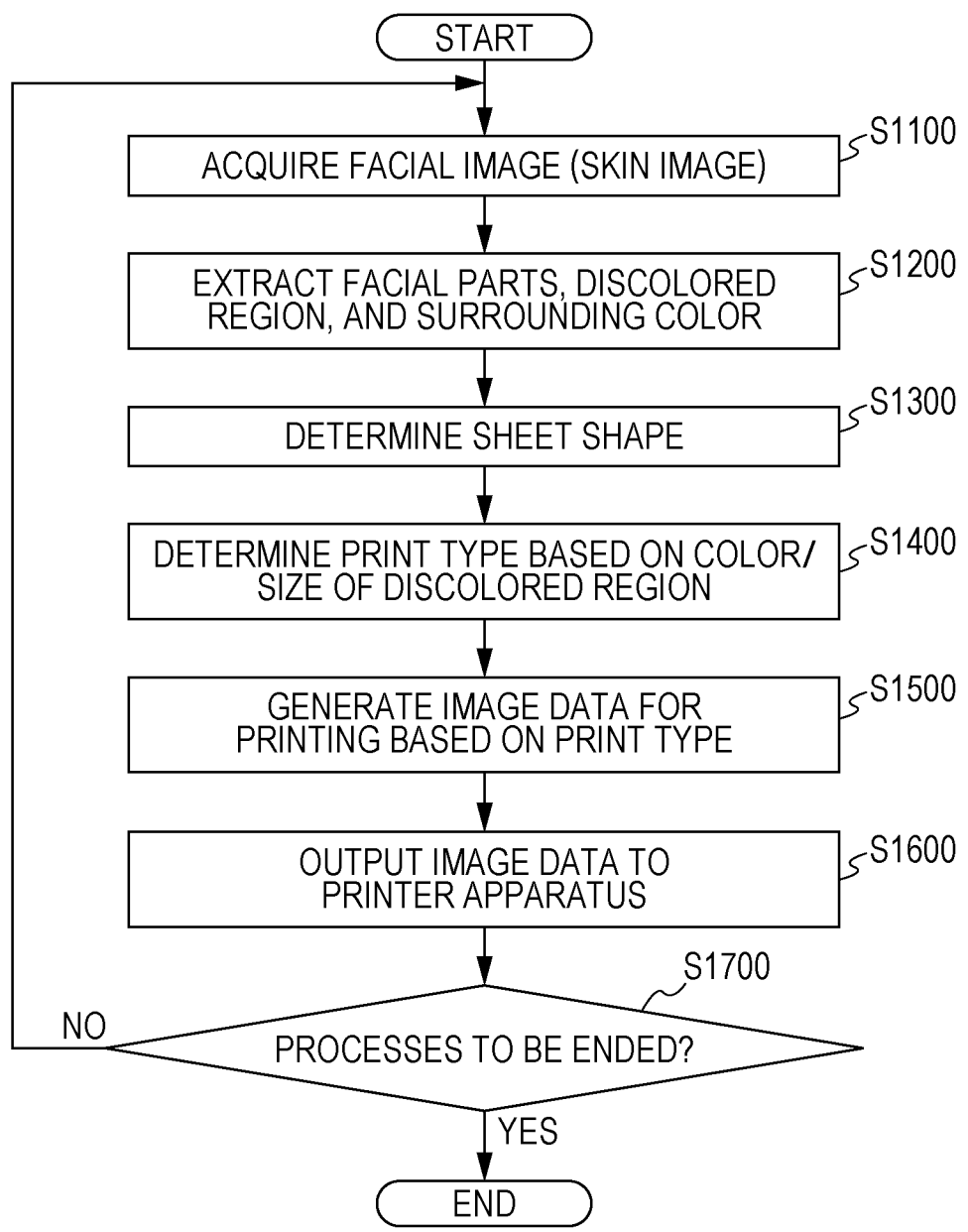

IMAGE PROCESSING APPARATUS, PRINTER APPARATUS, AND IMAGE PROCESSING METHOD

BACKGROUND

1. Technical Field

The present disclosure relates to an image processing apparatus and an image processing method for generating image data for printing an image on a sheet attachable to skin, and to a printer apparatus that performs the printing based on the image data.

2. Description of the Related Art

Conventionally, there exist techniques for making a discolored region of the skin, such as a spot on the cheeks, less noticeable (for example, see PTL 1). According to the technique described in PTL 1 (hereinafter referred to as "the conventional technique"), a discolored region of the skin is identified from a picked-up image of the skin, and a sheet attachable to the skin, on which a print material in the color of the non-discolored region is printed, is generated in size equal to or greater than that of the discolored region. Such a conventional technique can make the discolored region of the skin less noticeable by a simple work of attaching the sheet to the skin.

CITATION LIST

Patent Literature

PTL 1: Unexamined Japanese Patent Publication No. 2015-43836
PTL 2: Unexamined Japanese Patent Publication No. 2012-86475
PTL 3: Unexamined Japanese Patent Publication No. H10-46073
PTL 4: Unexamined Japanese Patent Publication No. 2005-126729
PTL 5: Unexamined Japanese Patent Publication No. 2012-203425
PTL 6: Unexamined Japanese Patent Publication No. 2003-44837

However, according to the conventional technique, a print material must be printed with a greater thickness in order to cover a deeply discolored region, which entails large consumption of the print material. In view of cost reduction and attaining of natural appearance, what is desired is the technique capable of making any discolored region of the skin less noticeable with a smaller amount of a print material.

SUMMARY

One non-limiting and exemplary embodiment provides an image processing apparatus, a printer apparatus, and an image processing method which are capable of making any discolored region of the skin less noticeable with a smaller amount of a print material.

In one general aspect, the techniques disclosed here feature an image processing apparatus that controls an operation of a printer apparatus printing an image on a sheet being attachable to skin, the image processing apparatus including: an image acquirer that acquires a skin image picked up from the skin; an image analyzer that extracts, from the skin image, a discolored region differing in color from surrounding skin by at least a predetermined level, and surrounding color being color of the skin surrounding the discolored region; a print type determiner that determines, based on at least one of color and size of the discolored region, a print type that includes at least one of use/nonuse of a base material containing a white pigment, a particle shape of a print material used in the printing, a scheme of the printing, and use/nonuse of lamé powder; and a printing controller that outputs, to the printer apparatus, image data having a content of printing a print material in the surrounding color, on a region corresponding to the discolored region in the sheet, and controls an operation of the printer apparatus according to the determined print type.

The present disclosure is capable of making any discolored region of the skin less noticeable with a smaller amount of a print material.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

It should be noted that general or specific embodiments may be implemented as a system, a method, an integrated circuit, a computer program, a storage medium, or any selective combination thereof.

BRIEF DESCRIPTION OF THE DRAWINGS

FIG. 7 shows exemplary base determining rule information according to the present disclosure;

FIG. 8 shows exemplary particle shape determining rule information according to the present disclosure;

FIG. 9 shows exemplary scheme determining rule information according to the present disclosure;

FIG. 10 shows exemplary lamé powder determining rule information according to the present disclosure; and FIG. 11 is a flowchart showing an exemplary operation of the image processing apparatus according to the present disclosure.

DETAILED DESCRIPTION

In the following, a detailed description will be given of one exemplary embodiment of the present disclosure with reference to the drawings.

System Structure

Firstly, a description will be given of the overview of a makeup supporting system that includes an image processing apparatus according to the present exemplary embodiment.

Figure 1:
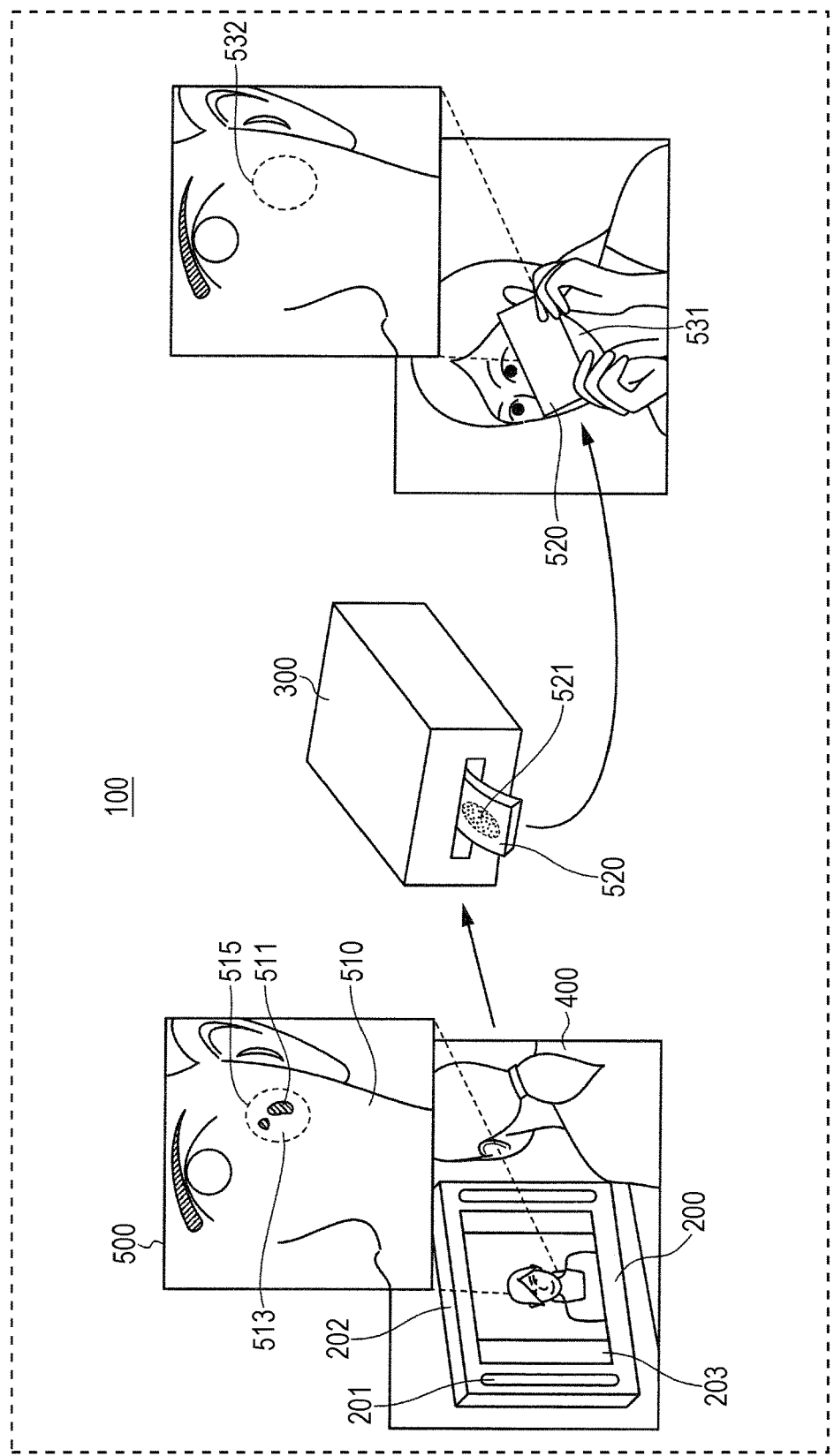
FIG. 1 is a schematic diagram showing the overview of an exemplary makeup supporting system according to the present disclosure.

FIG. 1 is a schematic diagram showing the overview of an exemplary makeup supporting system.

In FIG. 1, makeup supporting system 100 includes: image processing apparatus 200 that includes lighting 201, camera 202, and display 203 such as a liquid crystal display equipped with a touch panel; and printer apparatus 300 communicatively connected with image processing apparatus 200. Image processing apparatus 200 and printer apparatus 300 are disposed at, for example, a factory, a cosmetic shop, a beauty salon, a medical facility, a makeup room for grooming, an event site, or a home. Note that, image processing apparatus 200 may be a portable apparatus that can be carried with ease.

Image processing apparatus 200 picks up, with camera 202 disposed near display 203, an image of the face of user 400 positioned in front of display 203 with lighting 201 illuminated. Then, image processing apparatus 200 displays, on display 203, picked-up image 510 which is horizontally inverted (hereinafter referred to as "facial image 510"). That is, image processing apparatus 200 makes user 400 feel like looking in a mirror.

Further, image processing apparatus 200 extracts discolored region 511 in facial image 510 from the obtained facial image 500 (or from the image before inversion), and determines inclusive region 515 that includes discolored region 511. Then, image processing apparatus 200 generates image data of an image that forms a region in the color of surrounding 513 of discolored region 511 (hereinafter referred to as "the surrounding color") in the shape and size of inclusive region 515, and outputs the generated image data to printer apparatus 300.

The surrounding color may be determined by image processing apparatus 200 based on measured values of color information of an inclusive region or the like acquired with an external measurement device such as a spectrophotometer, or may be determined by selecting from a previously provided color sample. Alternatively, image processing apparatus 200 may acquire color information of the user's foundation, concealer or the like, and may determine the acquired color as the surrounding color. This may advantageously cause the surrounding color to excellently blend in terms of color with a cosmetic material used in conjunction with the makeup sheet.

Printer apparatus 300 prints an image on makeup sheet 520, which is attachable to skin 410, based on the image data output from image processing apparatus 200. For example, printer apparatus 300 prints an image on makeup sheet 520 being attached to a supporter (mat) which can be peeled off.

More specifically, printer apparatus 300 applies a pigment material (a cosmetic material or the like) similar in color to the surrounding color to a region corresponding to inclusive region 515, to generate makeup sheet 520 on which covering region (a shielding layer, a skin color correcting color layer) 521 is formed.

Makeup sheet 520 has a surface that is tightly attached to skin 410 (hereinafter referred to as "the skin-side surface"), and the opposite surface (hereinafter referred to as "the external surface"). Printer apparatus 300 prints covering region 521 on predetermined one of the skin-side surface and the external surface. For example, by being tightly attached to skin 410, makeup sheet 520 allows covering region 521 printed on the skin-side surface to be transferred to skin 410. Alternatively, by being maintained to be attached to skin 410, makeup sheet 520 allows covering region 521 printed on the skin-side surface or the external surface to be borne on skin 410.

As described above, covering region 521 is formed in the color of the skin surrounding discolored region 511. Accordingly, by being covered with covering region 521, in region 532 of the skin corresponding to inclusive region 515, discolored region 511 becomes less noticeable.

That is, makeup supporting system 100 realizes makeup of solving unevenness in color of skin 410 with a simple and quick operation of attaching makeup sheet 520 to skin 410.

Note that, makeup sheet 520 does not make the user feel uncomfortable when attached to the user's skin, and is nearly colorless and transparent, and biocompatible. Specifically, makeup sheet 520 is a thin film having a layer of biocompatible polymer of, for example, polylactic acid, polyglycolic acid, polycaprolactone, copolymer of the foregoing, hyaluronic acid, chitosan and the like, and having a thickness of 10 nm to 500 nm inclusive. A thin film that can be used as makeup sheet 520 is described in, for example, PTL 2, and therefore a detailed description thereof is not given herein.

Further, the print material (ink) used in printing by printer apparatus 300 and the specific structure of the members of printer apparatus 300 are described in, for example, PTL 3 to PTL 5, and therefore a detailed description thereof is not given herein.

The covering power (the effect of making a discolored region less noticeable) of covering region 521 to discolored region 511 largely differs depending on use/nonuse of a base material containing a white pigment, the particle shape of the print material, the printing scheme, and use/nonuse of lamé powder (hereinafter referred as "the print type" as appropriate). That is, a properly selected print type can enhance the covering power of covering region 521, and can sufficiently make any discolored region less noticeable with a smaller amount of a print material.

Here, a description will be given of the effect of use of a base material containing a white pigment.

Figure 2:
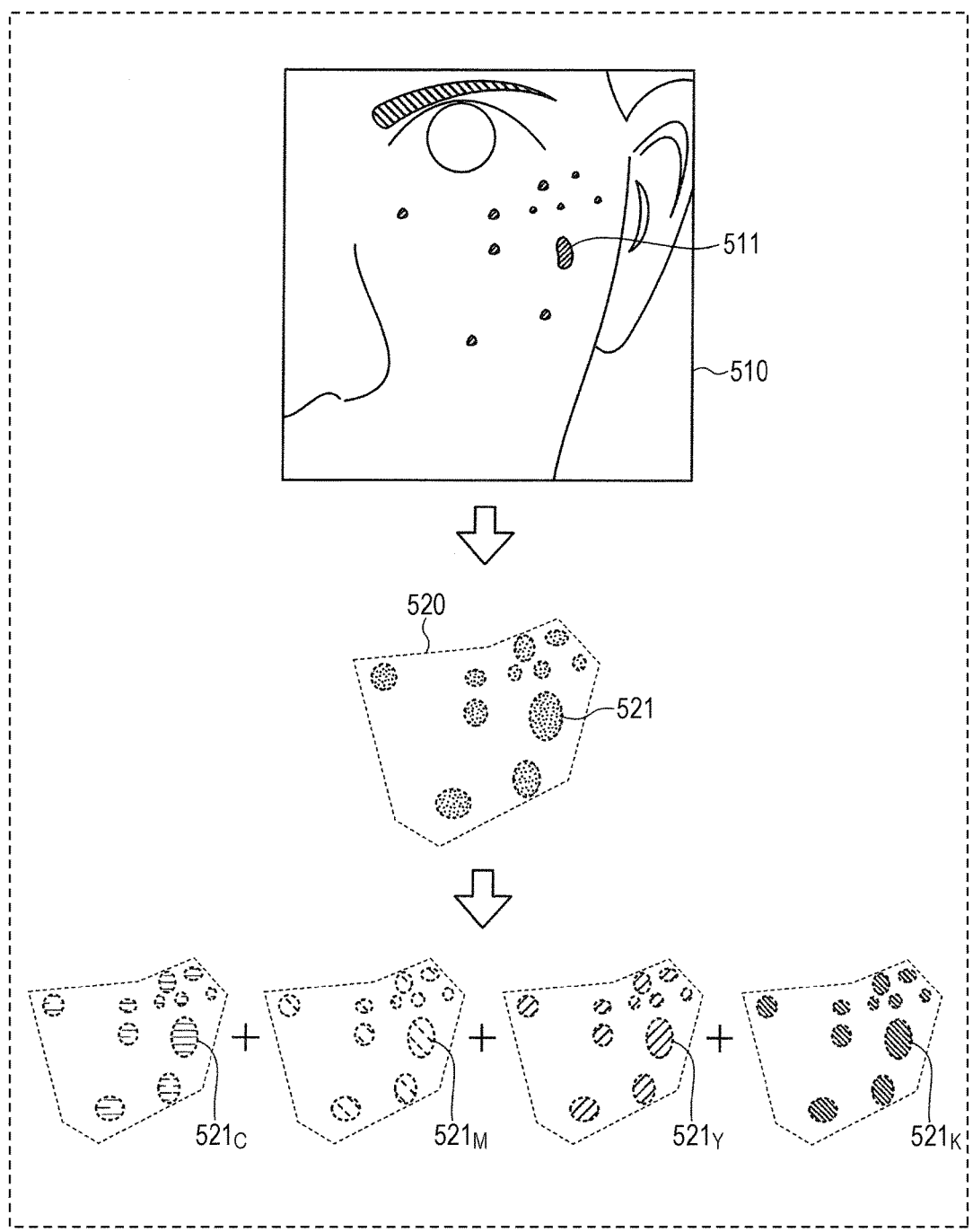
FIG. 2 is a schematic diagram showing an exemplary printing scheme according to the present disclosure.

FIG. 2 is a schematic diagram showing an exemplary printing scheme in forming covering region 521.

As shown in FIG. 2, based on discolored regions 511 extracted from facial image 510, it is determined to form covering region 521 in the surrounding color at the position corresponding to each discolored region 511 in makeup sheet 520. Printer apparatus 300 realizes any color (for example, the color of skin) by applying a pigment material (ink or the like) of limited colors, such as cyan (C), magenta (M), yellow (Y), and black (K).

More specifically, printer apparatus 300 performs printing by overlaying cyan covering region $521_C$, magenta covering region $521_M$, yellow covering region $521_Y$, and black covering region $521_K$ in their respective required densities, based on the image data.

On the other hand, since color mixing in printing is subtractive color mixing, there is limitation on the lightness of the color of covering region 521 that can be realized by printer apparatus 300. Further, provided that covering region 521 whose lightness is exactly identical to the surrounding color is formed, there still exists the following problem. That is, when the color of discolored region 511 is deep, that is, when the color of discolored region 511 differs largely from the surrounding color, the color of discolored region 511 is obviously seen through covering region 521 unless covering region 521 has a great thickness and is fully opaque.

Accordingly, for example when the color of discolored region 511 is deep, image processing apparatus 200 causes printer apparatus 300 to print on a region corresponding to covering region 521 in makeup sheet 520, adding a base material containing a white pigment. Note that, in the present exemplary embodiment, the term "white" refers to white color and any color closer to white color than the color of skin. Further, the depth of the color of discolored region 511 is, for example, the difference in color of discolored region 511 relative to the surrounding color, and is a distance on color coordinates in a predetermined color space such as RGB.

Figure 3:
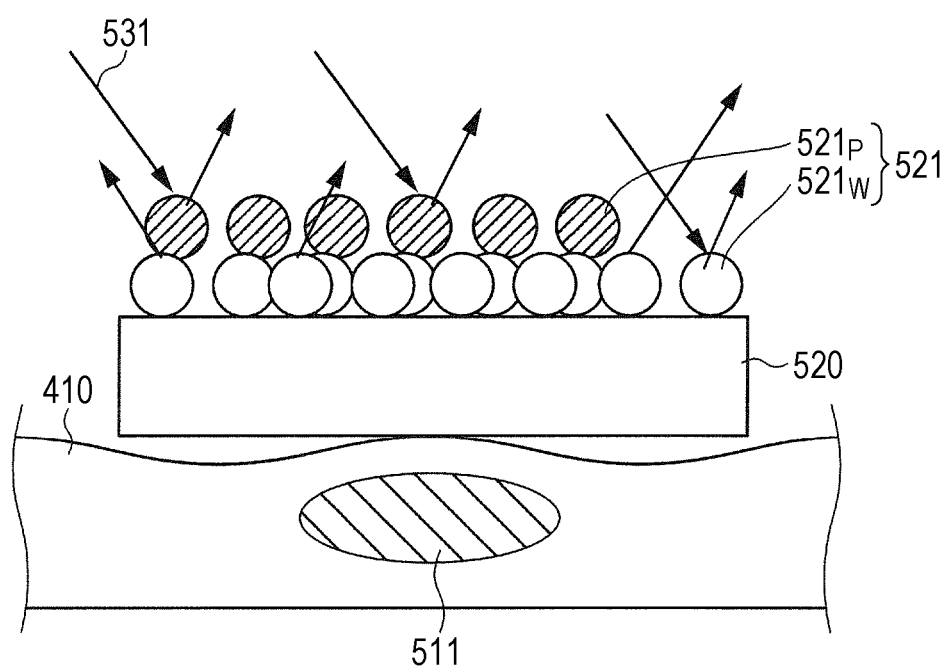
FIG. 3 is a schematic diagram for describing the effect exhibited by a base material containing a white pigment according to the present disclosure.

FIG. 3 is a schematic diagram for describing the effect attained by a base material containing a white pigment in covering region 521. FIG. 3 shows the cross section of the skin and makeup sheet 520.

As shown in FIG. 3, for example, on the external surface of makeup sheet 520, covering region 521 made up of pigment material $521_P$ closer in color to the surrounding color (hereinafter referred to as "the skin-color material") and pigment material $521_W$ closer in color to white color (hereinafter referred to as "the white-color material") is formed. Makeup sheet 520 is attached to skin 410 at the position where covering region 521 covers discolored region 511 of skin 410. In this state, white-color material $521_W$ is disposed between skin 410 and skin-color material $521_P$.

Incident light 531 from the outside world to covering region 521 is reflected by skin-color material $521_P$ or by white-color material $521_W$ positioned behind skin-color material $521_P$, to visualize their respective colors. That is, white color of white-color material $521_W$ is mixed with the color of skin-color material $521_P$, causing a color that is higher in lightness than the color of skin-color material $521_P$ to be visually recognized as the color of the entire covering region 521. Such an increase in lightness provides the effect of reducing the difference in lightness between the color of discolored region 511 and the surrounding color. Accordingly, a smaller amount of white-color material $521_W$ will suffice, relative to the required increase in amount of skin-color material $521_P$ for achieving the similar effect. Accordingly, addition of white-color material $521_W$ (the base material containing a white pigment) exhibits the effect of making discolored region 511 less noticeable while preventing an increase in the print material.

Note that, disposition of white-color material $521_W$ outer than skin-color material $521_P$ tends to cause the skin look unnaturally whitish. Accordingly, white-color material $521_W$ is desirably disposed nearer to skin 410 (on the inner side) than skin-color material $521_P$ is.

Figure 4:
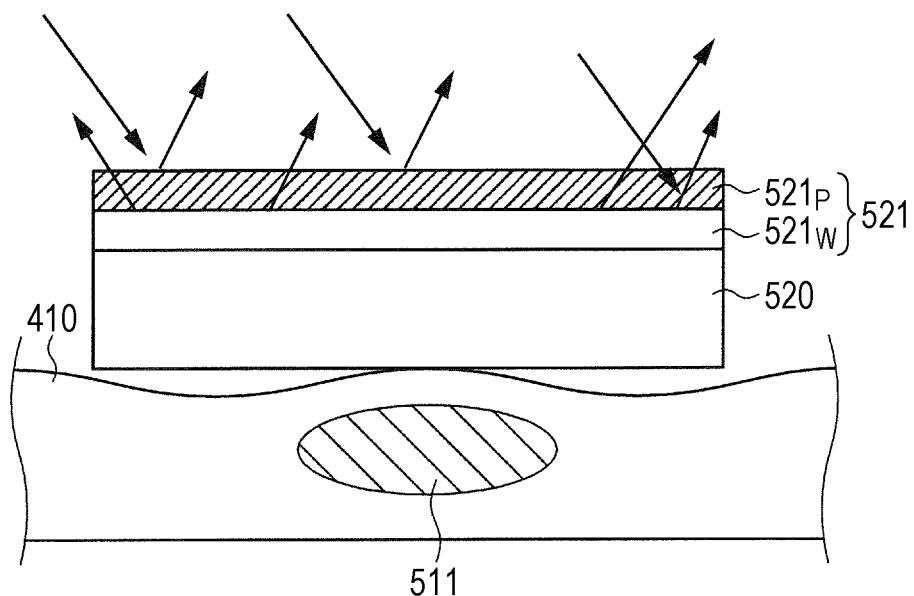
FIG. 4 is a diagram showing a first exemplary positional relationship between a white-color material and a skin-color material according to the present disclosure.

FIG. 4 is a diagram showing an exemplary positional relationship between white-color material $521_W$ and skin-color material $521_P$ in the case where covering region 521 is disposed at the external surface of makeup sheet 520. Further, FIG. 5 is a diagram showing an exemplary positional relationship between white-color material $521_W$ and skin-color material $521_P$ in the case where covering region 521 is disposed at the skin-side surface of makeup sheet 520.

In the case where covering region 521 is disposed at the external surface of makeup sheet 520, as shown in FIG. 4, printer apparatus 300 firstly prints white-color material $521_W$, and subsequently prints skin-color material $521_P$. Note that, makeup sheet 520 in such use has the bonding function (not shown) at the skin-side surface for causing makeup sheet 520 to be tightly attached to skin 410 for long hours. Therefore, makeup sheet 520 may have a thickness of 400 nm or greater. This tends to cause the unnatural whitish look due to white-color material $521_W$, and therefore it is important to dispose white-color material $521_W$ on the inner side.

Figure 5:
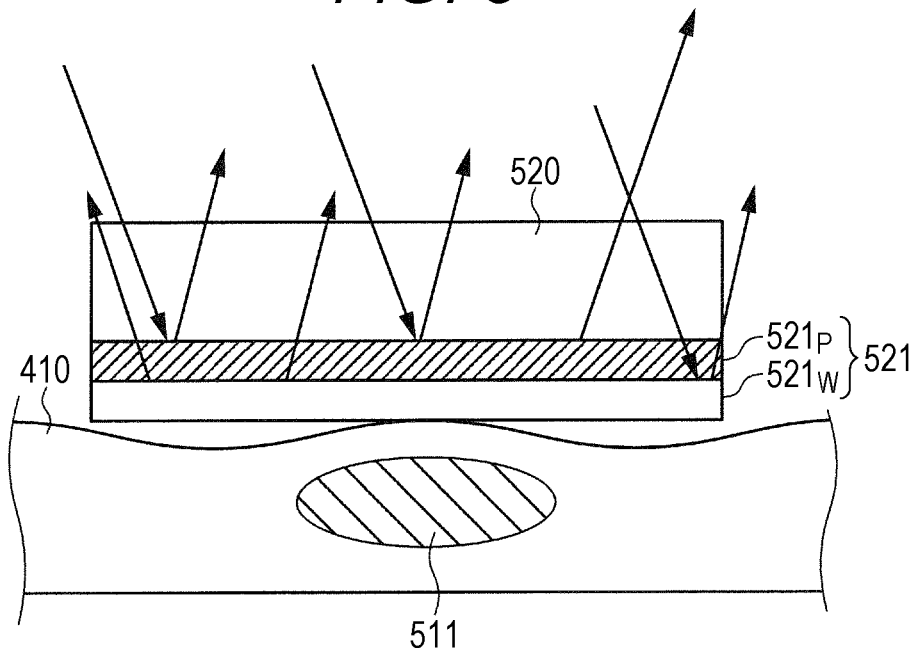
FIG. 5 is a diagram showing a second exemplary positional relationship between the white-color material and the skin-color material according to the present disclosure.

In the case where covering region 521 is disposed at the skin-side surface of makeup sheet 520, as shown in FIG. 5, printer apparatus 300 firstly prints skin-color material $521_P$, and subsequently prints white-color material $521_W$. Note that, in the case where covering region 521 is transferred to skin 410 with such makeup sheet 520, makeup sheet 520 may have a thickness of, for example, less than 400 nm.

Note that, in the present exemplary embodiment, discolored regions 511 being the target of extraction may differ from each other in the factor of discoloring. That is, discolored regions 511 are categorized, by the type of discoloring factor, into pigmented spots, chloasma, nevus spilus, melanocytic nevus, Nevus of Ota, acquired dermal melanocytosis, erythema, purpura, vitiligos, bruises, moles, dark pores, sunburned regions, acne (pimples), pimple marks, pigmentation caused by abrasion or irritation, wrinkles, ephelides (freckles), tattoos, verrucae, scars and the like.

Structure of Apparatus

Next, a description will be given of the structure of image processing apparatus 200.

Figure 6:
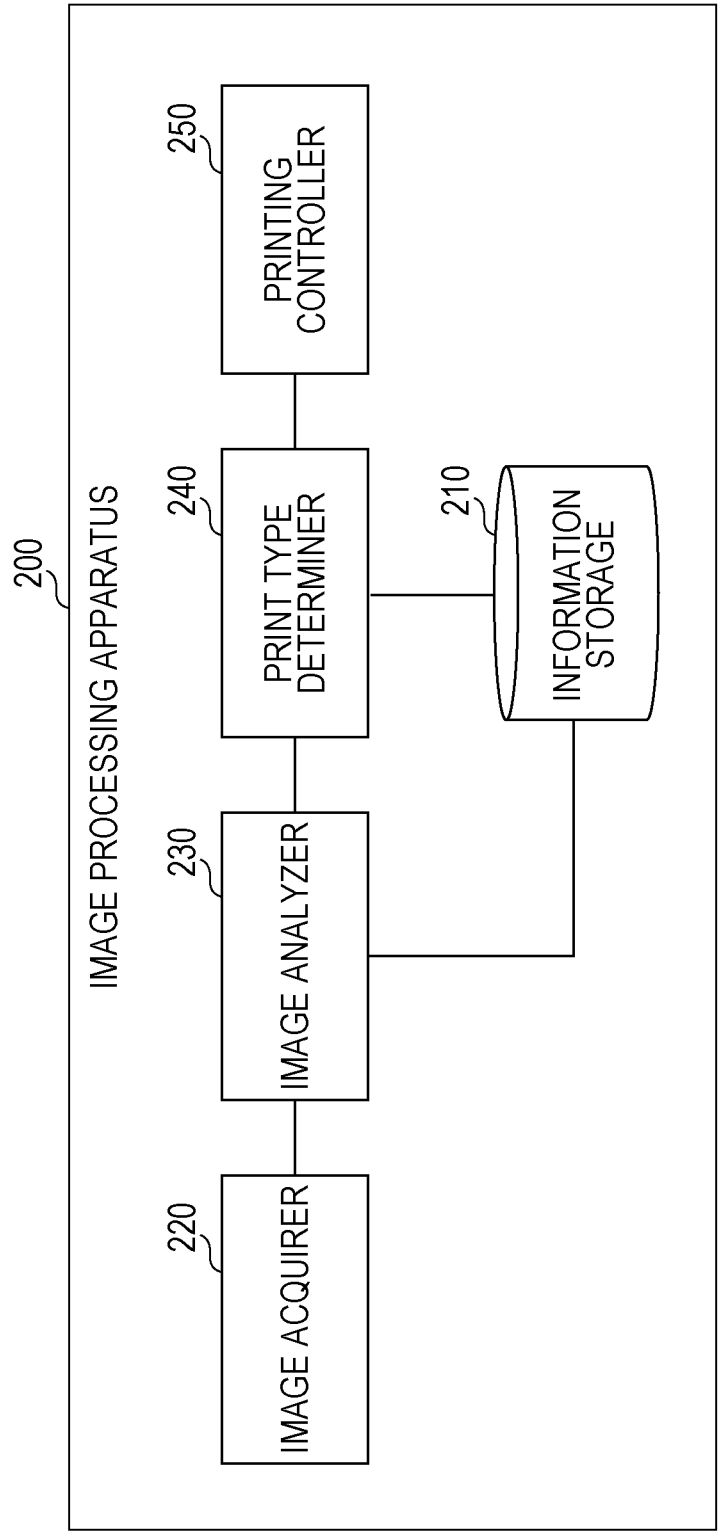
FIG. 6 is a block diagram showing an exemplary structure of an image processing apparatus according to the present disclosure.

FIG. 6 is a block diagram showing an exemplary structure of image processing apparatus 200.

In FIG. 6, image processing apparatus 200 includes information storage 210, image acquirer 220, image analyzer 230, print type determiner 240, and printing controller 250.

Information storage 210 previously stores various kinds of information necessary for image analyzer 230 to analyze an image, and various kinds of information necessary for print type determiner 240 to determine a print type.

Image acquirer 220 includes, for example, the above-described camera 202 (see FIG. 1), and picks up an image with camera 202. Image acquirer 220 outputs the picked-up image to image analyzer 230. The picked-up image may include a facial image picked up from the face, and a skin image picked up from the skin.

Image analyzer 230 extracts facial parts from a facial image picked up from the face, and extracts an image of a skin region (a skin image) from the facial image, based on the positions of the extracted facial parts in the facial image. Further, image analyzer 230 extracts, from the skin image, discolored region 511 differing in color from the surrounding skin by at least a predetermined level, and the color of the skin surrounding discolored region 511 (i.e., the surrounding color). Then, image analyzer 230 outputs, to print type determiner 240, analysis result information on the positions of the extracted facial parts, discolored region 511, and the surrounding color.

Print type determiner 240 determines, for each discolored region 511, inclusive region 515 that includes discolored region 511. Inclusive region 515, is, for example, an elliptical region that circumscribes discolored region 511. Further, print type determiner 240 determines a print type based on at least one of the color and size of discolored region 511 indicated by analysis result information. Here, the print type includes at least one of: use/nonuse of a base material containing a white pigment (white-color material $521_W$, see FIGS. 3 to 5); the particle shape of the employed print material; the printing scheme; and use/nonuse of lamé powder. Then, the print type determiner outputs the positions of the facial parts in the facial image, the position of inclusive region 515, and the determined print type to printing controller 250.

Print type determiner 240 performs the determination of the print type based on, for example, particle shape determining rule information, base determining rule information, scheme determining rule information, and lamé powder determining rule information stored in information storage 210. The particle shape determining rule information, the base determining rule information, the scheme determining rule information, and the lamé powder determining rule information will be detailed later.

Printing controller 250 outputs, to printer apparatus 300, image data having a content of printing a print material in the surrounding color to a region corresponding to discolored region 511 in makeup sheet 520, and controls the operation of printer apparatus 300 according to the determined print type. Printing controller 250 may perform the output of the image data to printer apparatus 300 and the operation control of printer apparatus 300 via wireless communication and/or wired communication, for example.

Note that, it is not essential for printing controller 250 to transmit the generated image data directly to printer apparatus 300, and may indirectly transmit the generated image data via other information recording device or the like. For example, printing controller 250 may record the generated image data on a recording medium such as a portable memory device, or may transmit the generated image data to a portable device (a smartphone, a tablet, a PC or the like). In this case, the user transmits the image data to printer apparatus 300 via the recording medium, the portable device or the like, and printing is appropriately performed as necessary based on a user's instruction or the like.

While not shown in the drawing, image processing apparatus 200 includes, for example, a CPU (a Central Processing Unit), a storage medium storing a control program such as ROM (Read Only Memory), working memory such as RAM (Random Access Memory), and a communication circuit. In this case, the functions of the units described above are realized by the CPU executing the control program.

Such image processing apparatus 200 can determine, based on at least one of the color and size of discolored region 511, use/nonuse of a base material containing a white pigment, the particle shape of a print material, the printing scheme, and use/nonuse of lamé powder.

Contents of Various Kinds of Information

Here, a description will be given of the content of each of the particle shape determining rule information, the base determining rule information, the scheme determining rule information, and the lamé powder determining rule information.

The particle shape determining rule information defines the determination criterion as to which print material of what particle shape is used, among print materials of different particle shapes. The base determining rule information defines the determination criterion as to whether or not to use a base material containing a white pigment. The scheme determining rule information defines the determination criterion as to which printing scheme is adopted, among a plurality of printing schemes. The lamé powder determining rule information defines the determination criterion as to whether or not to use lamé powder (a shimmering material).

FIG. 7 shows exemplary base determining rule information.

As shown in FIG. 7, base determining rule information 610 defines whether or not to use a base material containing a white pigment (hereinafter referred to as "the white-color base material" as appropriate) in association with the area of discolored region 511 and the difference in color depth relative to the adjacent discolored region. For example, in association with the condition "the color depth is less than a first predetermined value", the content "determine printing of a color material in the surrounding color" is described. In association with the condition "the color depth is equal to or greater than the first predetermined value", the content "determine printing of a white-color base material+a color material in the surrounding color" is described.

As has been described with reference to FIG. 3, addition of a base material containing a white pigment (white-color material $521_W$) can increase the lightness of covering region 521. Accordingly, for example, controlling the printing in accordance with base determining rule information 610 can improve the color covering power of covering region 521 to discolored region 511 while preventing an increase in thickness (application amount) of covering region 521.

Note that, base determining rule information 610 may define to form covering region 521 obtained by combining a skin-color material in a single color and thickness and a white-color material varying in color and thickness. That is, the layer of the white-color material and the layer of the skin-color material may not have one-to-one correspondence.

For example, when a plurality of discolored regions are adjacent to each other by a predetermined interval or smaller, base determining rule information 610 determines application range and thickness of a white-color material individually for each of the plurality of discolored regions, and determines a single skin-color material application range that includes such application ranges.

Here, the interval between a plurality of discolored regions is, for example, a minimum distance between discolored regions 511 on the facial surface, calculated from, for example, a pixel distance on the facial image, or a distance from camera 202 to the face of user 400 (see FIG. 1) and the pixel distance. The distance from camera 202 to the face of user 400 can be estimated from, for example, the parallax of the facial parts obtained with a stereo camera, the size of the face on the picked-up image, and sensor information from various kinds of distance sensors using infrared rays or ultrasounds. Alternatively, the distance from camera 202 to the face of user 400 can be obtained as follows. 3D scan data of the user's face including the face feature points and a measured distance between the feature points is previously acquired; and the distance from camera 202 to the face of user 400 is relatively obtained from the pixel distance between the feature points in the facial image acquired by image acquirer 220.

Such base determining rule information 610 can form a white-color material layer individually for each discolored region, and form a single skin-color material covering the plurality of discolored regions, to provide a single makeup sheet 520. That is, the present exemplary embodiment avoids troublesome work of attaching a makeup sheet to each of a plurality of adjacent discolored regions differing in color depth individually one by one, and allows such plurality of discolored regions to be covered easily. Further, provided that a plurality of makeup sheets 520 differing in base condition (the color or thickness of a white-color material or the like), that is, differing in degree of adjusting lightness are generated, with the plurality of makeup sheets 520 overlapping each other on the skin, the present exemplary embodiment can prevent an excessive increase in lightness in the overlapping parts.

FIG. 8 shows exemplary particle shape determining rule information.

As show in FIG. 8, particle shape determining rule information 620 defines use of a print material having a predetermined particle shape in association with the area of discolored region 511 and the color depth of discolored region 511. For example, in association with the condition "the area is less than a second predetermined value" and in association with the condition "the color depth is less than a third predetermined value", the content "select a print material of spherical crystal/indefinitely-shaped crystal" is described. Further, in association with the condition "the area is equal to or greater than the second predetermined value", and the condition "the color depth is equal to or greater than the third predetermined value", the content "select a print material of plate crystal" is described.

As used herein, "the area" is, for example, the area of discolored region 511 in the facial surface calculated from the number of pixels in the facial image, or from the distance from camera 202 to the face of user 400 and the pixel distance.

With the print material of spherical crystal/indefinitely-shaped crystal, printing can be performed with a higher degree of definition and uniform density, as compared to the print material of plate crystal. On the other hand, with the print material of plate crystal, printing over a wide area or of a great thickness can be performed in a shorter time, as compared to the print material of spherical crystal/indefinitely-shaped crystal. Accordingly, controlling the printing according to particle shape determining rule information 620 allows any print material to be applied to makeup sheet 520 with a proper thickness (application amount).

FIG. 9 shows exemplary scheme determining rule information.

As shown in FIG. 9, scheme determining rule information 630 defines the printing scheme to be employed, in association with the area of discolored region 511. For example, in association with the condition "the area is less than a fourth predetermined value", the content "select inkjet printing" is described, and in association with the condition "the area is equal to or greater than the fourth predetermined value", the content "select spray printing/relief printing" is described.

For inkjet printing, what is used is ink whose median value (median diameter (D50)) of the cumulative value of the particle size distribution measured by pigment laser diffraction is from 0.001 μm to 0.6 μm inclusive. Accordingly, inkjet printing can perform the printing with a higher degree of definition and uniform density, as compared to spray printing or relief printing. On the other hand, spray printing or relief printing can perform the printing over a wide area or of a great thickness in a shorter time, as compared to inkjet printing. Accordingly, controlling the printing according to scheme determining rule information 630 allows any print material to be applied to makeup sheet 520 with a proper thickness (application amount).

FIG. 10 shows exemplary lamé powder determining rule information.

As shown in FIG. 10, lamé powder determining rule information 640 defines whether or not to print lamé powder, in association with the area of discolored region 511. For example, in association with the condition "the area is equal to or greater than a fifth predetermined value", the content "determine printing of lamé powder" is described.

In the case where the area of discolored region 511 is great, adding lamé powder to provide a shine makes discolored region 511 less noticeable. Accordingly, controlling the printing in accordance with lamé powder determining rule information 640 can improve the color covering power of covering region 521 to discolored region 511 while preventing an increase in thickness (application amount) of covering region 521. Further, application of lamé powder exhibits the shimmering effect, which makes the skin look beautiful.

Note that, scheme determining rule information 630 described in FIG. 9 desirably further defines, in the case where a base material containing a white pigment is used, to apply the base material containing a white pigment (a shielding layer) by inkjet printing, and to print a pigment material in the surrounding color (skin-color ink) by spray printing.

Further, printer apparatus 300 that can selectively perform printing of various schemes is practically a large-sized apparatus that is installed in factory lines and supports various printing schemes. When printer apparatus 300 is an apparatus supporting gravure printing and inkjet printing, scheme determining rule information 630 may define, for example, a more complicated printing scheme.

Such a scheme may include: an upstream operation of performing gravure printing of a base material to provide a high shielding performance (increase thickness of the ink layer); a subsequent operation of performing inkjet printing of a skin-color material so that gradation is provided outward from the edge of the base material for causing covering region 521 to blend well with the skin in terms of color; and a downstream operation of performing spray printing with a shining material such as lamépowder. Such a printing scheme can generate makeup sheet 520 provided with a base material having a high shielding performance and yet blends well with the skin in terms of color.

Further, in the case where printer apparatus 300 is of a small size, being desktop and for home use, the suitable printing schemes for such printer apparatus 300 are inkjet printing and spray printing. Accordingly, in this case, scheme determining rule information 630 desirably defines a printing scheme in which inkjet printing and spray printing are combined. Note that, also in such a case, the shielding performance of covering region 521 can be improved by allowing the inkjet head or stage to scan for a plurality of times so that a print material forms layers.

Operation of Apparatus

Next, a description will be given of the operation of image processing apparatus 200.

FIG. 11 is a flowchart showing an exemplary operation of image processing apparatus 200.

In step S1100, image acquirer 220 acquires a facial image (a skin image).

In step S1200, image analyzer 230 extracts, from the facial image, the facial parts, discolored regions 511, and the surrounding color of each discolored region 511.

Specifically, for example, image analyzer 230 firstly acquires an image obtained by picking up an image of a predetermined color chart, and determines a correction value for color correction corresponding to the image pickup environment, based on the colors of the color chart in the image. Then, after performing color correction based on the determined correction value, image analyzer 230 detects the positions of the facial parts in the facial image by any known image recognition processing such as pattern matching. The scheme of extracting facial parts from an image is described in, for example, PTL 6, and therefore a detailed description thereof is not given herein.

Further, image analyzer 230 acquires, from the facial image excluding the facial parts, a region in a predetermined color range as a skin region. Image analyzer 230 then divides the skin region into discolored regions 511 and non-discolored region with reference to a predetermined pixel value (e.g., lightness), to extract discolored regions 511. Note that, here, image analyzer 230 may treat any discolored region 511 having an area equal to or smaller than a predetermined value as the non-discolored region. Then, image analyzer 230 extracts the average value of the non-discolored region near discolored regions 511 as the surrounding color. Note that, image analyzer 230 may extract discolored regions 511 and the surrounding color by the scheme described in PTL 1.

In step S1300, image analyzer 230 determines the sheet shape from the disposition of the facial parts. Specifically, image analyzer 230 determines, as the sheet shape, a closed shape capable of covering the extracted one or a plurality of discolored regions 511 (or regions greater than discolored regions 511 by a predetermined width) avoiding the positions of the facial parts (the nostrils, the eyes, the mouth, the eyebrows and the like) (for example, the shape such as makeup sheet 520 shown in FIGS. 2 to 6). Note that, since the face is three-dimensional and the sheet is basically two-dimensional, desirably the size of the sheet shape is limited to be equal to or smaller than 5 cm×5 cm, for example.

In step 1400, print type determiner 240 determines the print type based on at least one of the color and size of discolored region 511. That is, print type determiner 240 determines the print type based on the above-described particle shape determining rule information 620, base determining rule information 610, scheme determining rule information 630, and lamé powder determining rule information 640 (see FIGS. 7 to 10). Such a print type includes at least one of use/nonuse of a base material containing a white pigment, the particle shape of a print material in printing, the printing scheme, and use/nonuse of lamé powder.

Note that, print type determiner 240 may determine the print type based on just part of or all the above-described rules. Further, print type determiner 240 may accept a setting instruction from the user about based on what rule the print type should be determined. Further, print type determiner 240 may selectively adopt the rules according to the priorities previously set on the rules.

For example, print type determiner 240 acquires information indicative of the type of a printing facility used in printing makeup sheet 520, and preferentially selects the print type suitable for the type of the printing facility to be used.

Specifically, for example for a printing facility with limited selection of the printing scheme, such as just inkjet printing, print type determiner 240 determines the print type based on only base determining rule information 610 (see FIG. 7). Further, for a printing facility supporting a plurality of printing schemes such as inkjet printing and spray printing, print type determiner 240 selects the scheme based on scheme determining rule information 630 (see FIG. 9); determines use/nonuse of a base material containing a white pigment based on base determining rule information 610 (see FIG. 7); determines the particle shape based on particle shape determining rule information 620 (see FIG. 8); and determines use/nonuse of lamé powder based on lamé powder determining rule information 640 (see FIG. 10).

Further, for example, print type determiner 240 accepts an instruction specifying what condition is prioritized, among speed, quality, costs and the like, and preferentially selects the print type that satisfies the specified condition.

Specifically, when a higher priority is put on speed or costs, print type determiner 240 determines, on the premise that inkjet printing is performed, the print type adopting only base determining rule information 610 (see FIG. 7). Further, when a higher priority is put on quality, print type determiner 240 determines, on the premise that a plurality of schemes are used, use/nonuse of a base material containing a white pigment based on base determining rule information 610 (see FIG. 7); determines the particle shape based on particle shape determining rule information 620 (see FIG. 8); and determines use/nonuse of lamé powder based on lamé powder determining rule information 640 (see FIG. 10).

In step S1500, printing controller 250 generates image data having a content of printing a print material in the surrounding color on a region corresponding to discolored region 511 in makeup sheet 520. The image data is, for example, data of CMYK (Cyan, Magenta, Yellow, and Key plate) format. Further, based on the determined print type, printing controller 250 includes, in the image data, control information that instructs an operation according to the determined print type.

For example, printing controller 250 generates image data that instructs a two-step printing operation including: performing gravure printing with a white-color material on a region greater than covering region 521 (i.e., inclusive region 515); and subsequently performing inkjet printing with a skin-color material on a further greater region, so that the material fades at the outer circumference of such a region.

Note that, print type determiner 240 or printing controller 250 refers to a table (not shown) that is previously stored in information storage 210 and defines the correspondence between the difference in color (color difference) between the discolored region and the surrounding color and the application amount of the white-color material per unit area, and determines the application amount of the white-color material per unit area. Such a table associates, for example, the color difference and application density of the white-color material in linear relationship.

In step S1600, printing controller 250 outputs the generated image data to printer apparatus 300.

Further, in step S1700, image acquirer 220 determines whether or not it is instructed to end the processes by the user's operation or the like. When it is not instructed to end the processes (S1700: NO), image acquirer 220 returns the process to step S1100. Further, when it is instructed to end the processes (S1700: YES), image acquirer 220 ends the series of processes.

With such operations, image processing apparatus 200 can automatically extract discolored region 511 of the face, determine the print type based on the color/size of discolored region 511, and generate, using printer apparatus 300, makeup sheet 520 that efficiently covers discolored region 511. In particular, printing a white-color print material as the base of a skin-color print material, image processing apparatus 200 can easily form covering region 521 in arbitrary lightness, and can make a discolored region less noticeable even if the lightness of the discolored region is significantly low as compared to that of the surrounding color.

Effect of Present Exemplary Embodiment

As has been described above, image processing apparatus 200 according to the present exemplary embodiment controls an operation of printer apparatus 300 that prints an image on makeup sheet 520. Image processing apparatus 200 includes: image acquirer 220 that acquires a skin image; and image analyzer 230 that extracts, from the skin image, discolored region 511 and surrounding color being color of the skin surrounding discolored region 511. Image processing apparatus 200 further includes print type determiner 240 that determines, based on at least one of color and size of the discolored region, a print type that includes at least one of use/nonuse of a base material containing a white pigment, a particle shape of a print material used in the printing, a scheme of the printing, and use/nonuse of lamé powder. Image processing apparatus 200 further includes printing controller 250 that outputs, to printer apparatus 300, image data having a content of printing a print material in the surrounding color, on a region corresponding to the discolored region in makeup sheet 520, and controls an operation of printer apparatus 300 according to the determined print type.

Thus, image processing apparatus 200 according to the present exemplary embodiment can change the print type applied to discolored region 511 according to the color or size of discolored region 511. Depending on the color or size of discolored region 511, a change in the print type may achieve the similar covering effect with a reduced application amount of the print material. Accordingly, image processing apparatus 200 can make discolored region 511 of skin less noticeable with a smaller amount of the print material.

Variation of Present Exemplary Embodiment

Note that, the scheme of extracting discolored region 511, the scheme of determining the print type, and the printing scheme are not limited to those described in the foregoing. For example, as the scheme of extracting discolored region 511 and the scheme of determining the print type, known classification scheme, pattern recognition scheme, clustering scheme, and optimization scheme can be employed.

The known classification scheme may be, for example, the decision tree analysis, the neural networks (including deep learning), and the naive Bayes. The known pattern recognition scheme may be, for example, the neural networks (including deep learning) and the support vector machine (SVM). The known clustering scheme may be, for example, the k-Nearest Neighbor (k-NN), the k-means, and the hierarchical clustering. The known optimization scheme may be, for example, the genetic algorithm.

Further, the selectable print type is not limited to the foregoing example. For example, the selectable print scheme may include inkjet printing, spray printing, gravure printing, relief printing, flexography, silk-screen printing, pad printing, thermal printing, elcography, toner jet, magnetography, and ionography. Still further, for example, the selectable white-color material may include titanium oxide, barium sulfate, and calcium carbonate. Still further, the selectable particle shape of the print material may include, for example, an acicular shape, an indefinite shape, a spherical shape, and a plate shape.

Still further, the scheme of determining the sheet shape is not limited to the foregoing example. For example, image analyzer 230 may form a handle for the user to grasp makeup sheet 520, at part of makeup sheet 520 excluding covering region 521.

Still further, the scheme of generating image data is not limited to the foregoing example. For example, image analyzer 230 may acquire the face feature points such as the corners of the eyes and the corners of the mouth, and may determine the shape of the makeup sheet that is extended to the positions in close proximity to these face feature points. Further, printing controller 250 may generate image data having a content of printing, on makeup sheet 520, markers for alignment with the face feature points. Note that, when makeup sheet 520 that is kept applied on the skin is employed, desirably, the markers are printed on the supporter which is nearly colorless and transparent, or may be made of a material that becomes invisible with time by temperatures or drying.

Still further, an image processed by image processing apparatus 200 is not limited to a facial image, and may be, for example, an image picked up from the back of the hand or the skin of the arm.

Still further, part of the structure of image processing apparatus 200 may be physically separated from other part of image processing apparatus 200. In this case, each of these plurality of separated parts must be equipped with a communicator for establishing communication with each other. For example, part of the functions of image processing apparatus 200 may be implemented by cloud migration. Further, image processing apparatus 200 and printer apparatus 300 may be integrally structured. Still further, disposition of image processing apparatus 200 and printer apparatus 300 is not limited to the foregoing example. For example, printer apparatus 300 may be disposed remotely from image processing apparatus 200, such as at a printing factory, and may receive image data via a communication network such as the Internet.

Summary of Present Disclosure

An image processing apparatus of the present disclosure controls an operation of a printer apparatus that prints an image on a sheet being attachable to skin, the image processing apparatus including: an image acquirer that acquires a skin image picked up from the skin; an image analyzer that extracts, from the skin image, a discolored region differing in color from surrounding skin by at least a predetermined level, and surrounding color being color of the skin surrounding the discolored region; a print type determiner that determines, based on at least one of color and size of the discolored region, a print type that includes at least one of use/nonuse of a base material containing a white pigment, a particle shape of a print material used in the printing, a scheme of the printing, and use/nonuse of lamé powder; and a printing controller that outputs, to the printer apparatus, image data having a content of printing a print material in the surrounding color, on a region corresponding to the discolored region in the sheet, and controls an operation of the printer apparatus according to the determined print type.

Note that, in the image processing apparatus, the print type determiner may preferentially select, on condition that an area of the discolored region is at least a predetermined value, a print material of spherical crystal/indefinitely-shaped crystal, and may preferentially select, on condition that the area of the discolored region is less than the predetermined value, a print material of a plate crystal.

Further, in the image processing apparatus, the print type determiner may determine, on condition that color depth of the discolored region is at least a predetermined level, to print a white-color print material as a base of the print material in the surrounding color.

Still further, in the image processing apparatus, the print type determiner may determine, on condition that a difference in color depth between a plurality of adjacent ones of the discolored regions is at least a predetermined level, to print a white-color print material as a base of the print material in the surrounding color.

Still further, in the image processing apparatus, the print type determiner may preferentially select, on condition that an area of the discolored region is at least a predetermined value, spray printing/relief printing, and may preferentially select, on condition that the area of the discolored region is less than the predetermined value, inkjet printing.

Still further, in the image processing apparatus, the print type determiner may determine, on condition that an area of the discolored region is at least a predetermined value, to print using the lamé powder.

A printer apparatus of the present disclosure prints an image on a sheet being attachable to skin, the printer apparatus including: an information acquirer that acquires a print type that includes at least one of use/nonuse of a base material containing a white pigment, a particle shape of a print material used in the printing, a scheme of the printing, and use/nonuse of lamé powder, the print type being determined based on at least one of color and size of a discolored region in the skin differing in color from surrounding skin by at least a predetermined level, and the image data having a content of printing a print material in surrounding color being color of the skin surrounding the discolored region, on a region corresponding to the discolored region in the sheet; and a printing processor that performs printing indicated by the image data, by operating according to the acquired print type.

An image processing method of the present disclosure controls an operation of a printer apparatus that prints an image on a sheet being attachable to skin, the image processing method including: acquiring a skin image picked up from the skin; extracting, from the skin image, a discolored region differing in color from surrounding skin by at least a predetermined level, and surrounding color being color of the skin surrounding the discolored region; determining, based on at least one of color and size of the discolored region, a print type that includes at least one of use/nonuse of a base material containing a white pigment, a particle shape of a print material used in the printing, a scheme of the printing, and use/nonuse of lamé powder; and outputting, to the printer apparatus, image data having a content of printing a print material in the surrounding color, on a region corresponding to the discolored region in the sheet, and controlling an operation of the printer apparatus according to the determined print type.

The image processing apparatus, the printer apparatus, and the image processing method according to the present disclosure are useful as an image processing apparatus, a printer apparatus, and an image processing method that make any discolored region of the skin less noticeable with a smaller amount of a print material.

What is claimed is:

1. An image processing apparatus that controls an operation of a printer apparatus printing an image on a sheet being attachable to skin, the image processing apparatus comprising:
    an image acquirer that acquires a skin image picked up from the skin;
    an image analyzer that extracts, from the skin image corresponding to the area that is printed on the sheet, a discolored region differing in color from surrounding skin by at least a predetermined level, and surrounding color being color of the skin surrounding the discolored region that is inside of the area that is printed on the sheet;
    a print type determiner that determines, based on at least one of color and size of the discolored region, a print type that includes at least one of use or nonuse of a base material containing a white pigment, a particle shape of a print material used in the printing, a scheme of the printing, and a use or non-use of shimmering material; and
    a printing controller that outputs, to the printer apparatus, image data having a content of printing a print material in the surrounding color, on a region corresponding to the discolored region inside the sheet, and controls an operation of the printer apparatus according to the determined print type,
    wherein the print type determiner also determines an amount of white-color material per unit area based on a color difference between the discolored region and the surrounding color.

2. The image processing apparatus according to claim 1, wherein the print type determiner selects, on condition that an area of the discolored region is at least a predetermined value, a print material of spherical crystal or indefinitely-shaped crystal, and selects, on condition that the area of the discolored region is less than the predetermined value, a print material of a plate crystal.

3. The image processing apparatus according to claim 1, wherein the print type determiner determines, on condition that color depth of the discolored region is at least a predetermined level, to print a white-color print material as a base of the print material in the surrounding color.

4. The image processing apparatus according to claim 1, wherein the print type determiner determines, on condition that a difference in color depth between a plurality of adjacent ones of the discolored regions is at least a predetermined level, to print a white-color print material as a base of the print material in the surrounding color.

5. The image processing apparatus according to claim 1, wherein the print type determiner selects, on condition that an area of the discolored region is at least a predetermined value, spray printing or relief printing, and selects, on condition that the area of the discolored region is less than the predetermined value, inkjet printing.

6. The image processing apparatus according to claim 1, wherein the print type determiner determines, in the case of an area of the discolored region is larger than a predetermined value, to print using the shimmering material.

7. The image processing apparatus according to claim 1, wherein a layer of the surrounding color is laminated printed on a layer of white-color.

8. The image processing apparatus according to claim 1, wherein a relationship between the color difference and a density of the white-color material is defined as linear.

9. A printer apparatus that prints an image on a sheet being attachable to skin, the printer apparatus comprising:
    an information acquirer that acquires a print type that includes at least one of use or nonuse of a base material containing a white pigment, a particle shape of a print material used in the printing, a scheme of the printing, and a use or non-use of shimmering material, the print type being determined based on at least one of color and size of a discolored region in the skin corresponding to the area that is printed on the sheet, the discolored region differing in color from surrounding skin by at least a predetermined level, and the image data having a content of printing a print material in surrounding color being color of the skin surrounding the discolored region, on a region corresponding to the discolored region in the sheet; and
    a printing processor that performs printing indicated by the image data, by operating according to the acquired print type,
    wherein determining the print type also includes determining an amount of white-color material per unit area based on a color difference between the discolored region and the surrounding color.

10. An image processing method for controlling an operation of a printer apparatus that prints an image on a sheet being attachable to skin, the image processing method comprising:

acquiring a skin image picked up from the skin;

extracting, from the skin image corresponding to the area that is printed on the sheet, a discolored region differing in color from surrounding skin by at least a predetermined level, and surrounding color being color of the skin surrounding the discolored region that is inside of the area that is printed on the sheet;

determining, based on at least one of color and size of the discolored region, a print type that includes at least one of use or nonuse of a base material containing a white pigment, a particle shape of a print material used in the printing, a scheme of the printing, and a use or non-use of shimmering material; and outputting, to the printer apparatus, image data having a content of printing a print material in the surrounding color, on a region corresponding to the discolored region inside the sheet, and controlling an operation of the printer apparatus according to the determined print type, wherein the determining also includes determining amount of white-color material per unit area based a color difference between the discolored region and the surrounding color.

\* \* \* \* \*